US006835549B2

(12) United States Patent  
Das

(10) Patent No.: US 6,835,549 B2  
(45) Date of Patent: Dec. 28, 2004

(54) IMMUNOASSAY METHOD FOR THE DIAGNOSIS OF GASTRIC INTESTINAL METAPLASIA ASSOCIATED WITH GASTRIC CARCINOMA

(75) Inventor: Kiron M. Das, Martinsville, NJ (US)

(73) Assignee: University of Medicine & Dentistry of New Jersey, Newark, NJ (US)

( * ) Notice: Subject to any disclaimer, the term of this patent is extended or adjusted under 35 U.S.C. 154(b) by 0 days.

(21) Appl. No.: 09/512,515

(22) Filed: Feb. 24, 2000

(65) Prior Publication Data

US 2003/0077675 A1 Apr. 24, 2003

(51) Int. Cl.$^7$ .............................................. G01N 33/53
(52) U.S. Cl. ..................... 435/7.23; 435/7.9; 435/7.92; 436/64; 436/503
(58) Field of Search ................................. 435/7.23, 7.9, 435/7.92; 436/64, 503

(56) References Cited

PUBLICATIONS

Stedman's Medical Dictionary, 27$^{th}$ Edition, Lippincott Williams & Wilkens, 2000, Medical Economics Company, Inc., Montvale, N.J., 2002.*
Pantuck et al. British Journal of Urology 82:426–430, 1998.*
Babaev et al. Database Medline on Dialog, 03905999, Arkhiv Patolgii, 45/1:76–78, 1983.*
Petersen et al. Database Medline on Dialog, 05813907, Journal of Histochemistry and Cytochemistry 34/6:801–809, Jun. 1986.*
Pinkus et al. Database Medline on Dialog, 06042776, Journal of Histochemistry and Cytochemistry, 33/5:465–473, May 1985.*
Griffel et al., Digestive Diseases and Sciences, 45(1):40–48, Jan. 2000.*
Gujral et al., Gastroenterology 106/4, Part 2, Apr. 1994.*
Garewal et al. Gastroenterology 112 (4 SUPPL.):pA567, 1997.*
Badve et al. Hepatology 28/4:523A, Nov. 1998.*
Das et al., "Detection of a Shared Colon Epithelial Epitope on Barrett Epithelium by a Novel Monoclonal Antibody," Annals of Internal Medicine, vol. 120, No. 9, (May 1, 1994) pp. 753–756.
Das et al., "The Production and Characterization of Monoclonal Antibodies to a Human Colonic Antigen Associated with Ulcerative Colitis: Cellular Localization of the Antigen by Using the Monoclonal Antibody," J. Immunol., vol. 139, No. 1 (Jul. 1, 1987) p. 77–84.

* cited by examiner

Primary Examiner—Sheela J. Huff
(74) Attorney, Agent, or Firm—Licata & Tyrrell P.C.

(57) ABSTRACT

This invention pertains to an in vitro immunoassay method for diagnosing human gastric intestinal metaplasia which comprises the steps of (a) contacting a gastric tissue sample of a subject suspected of having human gastric intestinal metaplasia cells with the monoclonal antibody DAS-1, or a fragment thereof, which monoclonal antibody is produced by the hybridoma deposited under ATCC accession number HB 9397 and which reacts with human gastric intestinal metaplasia antigen; and (b) detecting immunoreactivity between the gastric tissue and the monoclonal antibody, such immunoreactivity indicating a positive diagnosis of human gastric intestinal metaplasia. This invention also pertains to an in vivo immunoassay method for diagnosing human gastric intestinal metaplasia which comprises the steps of (a) administering to a human, suspected of having human gastric intestinal metaplasia, the monoclonal antibody DAS-1, or a fragment thereof, which monoclonal antibody is produced by the hybridoma deposited under ATCC accession number HB 9397 and which reacts with human gastric intestinal metaplasia antigen and is tagged with an isotope; and (b) detecting immunoreactivity between the human gastric intestinal metaplasia cells and the monoclonal antibody by external scanning, such immunoreactivity indicating a positive diagnosis of human gastric intestinal metaplasia.

19 Claims, No Drawings

IMMUNOASSAY METHOD FOR THE DIAGNOSIS OF GASTRIC INTESTINAL METAPLASIA ASSOCIATED WITH GASTRIC CARCINOMA

BACKGROUND OF THE INVENTION

1. Field of the Invention

This invention pertains to an in vitro immunoassay method for diagnosing human gastric intestinal metaplasia which comprises the steps of (a) contacting a gastric tissue sample of a subject suspected of having human gastric intestinal metaplasia cells with the monoclonal antibody DAS-1, or a fragment thereof, which monoclonal antibody is produced by the hybridoma deposited under ATCC accession number HB 9397 and which reacts with human gastric intestinal metaplasia antigen; and (b) detecting immunoreactivity between the gastric tissue and the monoclonal antibody, such immunoreactivity indicating a positive diagnosis of human gastric intestinal metaplasia. This invention also pertains to an in vivo immunoassay method for diagnosing human gastric intestinal metaplasia which comprises the steps of (a) administering to a human, suspected of having human gastric intestinal metaplasia, the monoclonal antibody DAS-1, or a fragment thereof, which monoclonal antibody is produced by the hybridoma deposited under ATCC accession number HB 9397 and which reacts with human gastric intestinal metaplasia antigen and is tagged with an isotope; and (b) detecting immunoreactivity between the human gastric intestinal metaplasia cells and the monoclonal antibody by external scanning, such immunoreactivity indicating a positive diagnosis of human gastric intestinal metaplasia.

2. Description of the Background

Gastric carcinoma remains the second most common cause of cancer deaths in the world. In some of the developing countries, gastric carcinoma is the leading cause of human cancer. The cause of this increase, particularly in the developing countries, is not clear, however, *Helicobacter pylori* (*H. Pylori*) infection has been considered to be a risk factor for gastric carcinoma by the World Health Organization on the basis of several studies all over the world (Parsonnet et al., New Engl J Med 325:1127–1131 (1991)). It is well established that gastric intestinal metaplasia is a pre-cancerous condition, however, it is not known whether there is a sub-group of patients with gastric intestinal metaplasia who are more prone to cancer. Some literature suggests that gastric intestinal metaplasia with colonic phenotype of metaplasia changes is more prone to cancer and other literature suggests that small intestinal metaplastic changes are more prone to cancer.

In addition to the fully developed intestinal metaplasia, cellular variants suggesting partial or incomplete forms of metaplasia were observed in both the benign and the malignant cells, Goldman et al., Laboratory Investigation, 18, 203–210 (1968). The tumor cells exhibited alterations in the surface microvilli, terminal webs, mucin granules, plasma membranes, and nuclei, as well as the presence of large lysosomal structures. A correlative study between the morphology and the staining reactions of the mucin granules in 1 u sections was undertaken. In the normal foveolar and surface mucous cells, these granules were dark and small and stained strongly with periodic acid, Schiff only, whereas the pale granules in the mature goblet cells reacted with Alcian Blue as well. No such correlation could be made in the benign cells with partial metaplasia and in the tumor cells. The metaplastic cells however resembled those seen in the small intestine and paneth cells were present as well. Earlier studies using various enzyme histochemistry also suggested that metaplasia associated with carcinoma are identical to small intestine. Planteydt et al. J. Path. Bact. 80:317–323 (1960)).

Gastric atrophy and intestinal metaplasia are considered the earliest phenotypic changes in the cascade of events leading from normal mucosa to intestinal-type gastric cancer, and epidemiological evidence links *Helicobacter pylori* to gastric epithelial malignancies. Rugge et al., Digestive Diseases and Sciences, 41, 950–955 (1996). To evaluate any causal relationship between bacterial infection and atrophic metaplastic lesions, gastric pathology was histologically and histochemically evaluated in 267 consecutive, non-ulcerous, untreated subjects, with attention given to the phenotypes of intestinal metaplasia. The prevalence of *Helicobacter pylori* infection was 61%. Intestinal metaplasia (particularly types II and III), suggestive of colonic phenotype, was significantly associated with both *Helicobacter pylori* detection and increasing age. The development of intestinal metaplasia proved more significantly linked with *Helicobacter pylori* infection than with age with no interaction. *Helicobacter pylori* can be considered among the major causal agents of mucosal lesions involved in the multistep process of gastric carcinogenesis justifying an attempt to eradicate this bacterial infection.

Using hybridoma technology, a monoclonal antibody ($7E_{12}H_{12}$, IgM isotype) was developed against a colon epithelial antigen associated with ulcerative colitis (Das et al., J. Immunol. 139:77, 1987). The monoclonal antibody $7E_{12}H_{12}$ binds specifically to colonocytes along baso-lateral and brush border areas and it does not react with 13 other epithelial organs or any other parts of the gastrointestinal tract including the esophagus, stomach, and small intestine.

The colon epithial specific protein (CEP) recognized by $7E_{12}H_{12}$ mAb was predominantly localized at the plasma membrane in the apical (brush border area) and basolaceral domains of colonocytes (Das, K. M. et al., J. Immunol. 1987;139:77–84). Using two and three color immunofluorescence assay (Halstensen, T. S. et al., Gut 1993;34:650–657), the $7E_{12}H_{12}$ reactive epitope was also localized exclusively in colonic enterocytes, but not in small intestinal enterocytes, with increasing intensity caudally, expanding to intense cytoplasmic expression in the rectum. However, the mAb DAS-1 antibody has been shown to react with several precancerous conditions such as Barrett's Epithelium and chronic cystitis profunda, U.S. Pat. No. 5,888,743, Pantuck et al., J. Urol., 158, 1722 (1977). However, the mAb DAS-1 antibody does not react with normal gastroesophageal mucosa and normal urinary bladder but does react with adenocarcinoma from Barrett's Epithelium and urinary bladder carcinoma.

SUMMARY OF THE INVENTION

The present invention pertains to an in vitro immunoassay method for diagnosing human gastric intestinal metaplasia which comprises the steps of:

(a) contacting a gastric tissue sample of a subject suspected of having human gastric intestinal metaplasia cells with the monoclonal antibody DAS-1, or a fragment thereof, which monoclonal antibody is produced by the hybridoma deposited under ATCC accession number HB 9397 and which reacts with human gastric intestinal metaplasia antigen; and (b) detecting immunoreactivity between the gastric tissue and the monoclonal antibody, such immunoreactivity indicating a positive diagnosis of human gastric intestinal metaplasia.

Preferably, the human gastric intestinal metaplasia antigen is colon epithial specific protein.

Preferably, the antibody or fragment is directly or indirectly attached to a detectable label. Preferably detecting immunoreactivity is performed by immunoperoxidase staining, immunofluorescence, immunoelectronmicroscopy, or ELISA, and more preferably the immunoassay method is immunoperoxidase staining. Most preferably, the immunoperoxidase staining comprises (a) deparaffinizing the intestinal tissue by heating; (b) immersing the deparaffinized tissue in xylene; (c) rehydrating the tissue in decreasing concentrations of alcohol; (d) washing the rehydrated tissue in neutral PBS; (e) reducing the aldehydes of the washed tissue of step (d); (f) reacting the tissue with normal goat serum, the monoclonal antibody, biotinylated goat anti-mouse antibody and avidin-biotin-peroxidase complex; (g) treating the reacted tissue with diaminobenzidine; (h) washing the diaminobenzidine-treated tissue; (i) staining the washed tissue of step (h) with hematoxylin, eosin or both; and (j) examining the stained tissue under a microscope to detect the presence of immunoreactivity. The immunoperoxidase staining may further comprise the step of trypsinizing the intestinal tissue after reducing the aldehydes in the tissue but before reacting the tissue with the goat serum, monoclonal antibody, biotinylated goat anti-mouse antibody and avidin-biotin-peroxidase complex. The decreasing concentrations of alcohol used for rehydration may be 100%, 95%, 70%, and 50% alcohol.

The method may further comprise the step of performing a negative control assay on a negative control sample to detect human gastric intestinal metaplasia cells present in the negative control sample and comparing results of the assay in (b) with the results of the negative control assay, wherein the presence of human gastric intestinal metaplasia cells in the assay in (b) above the presence of human gastric intestinal metaplasia cells in the negative control assay indicates a positive diagnosis of human gastric intestinal metaplasia. The method may also further comprise the step of performing a positive control assay on a positive control sample to detect human gastric intestinal metaplasia cells present in the positive control sample.

The present invention also pertains to an in vitro immunoassay method for screening for human gastric intestinal metaplasia, thereby indicating a predisposition for gastric carcinoma, which comprises the steps of:
(a) contacting a gastric tissue sample of a subject suspected of having human gastric intestinal metaplasia cells with the monoclonal antibody DAS-1, or a fragment thereof, which monoclonal antibody is produced by the hybridoma deposited under ATCC accession number HB 9397 and which reacts with human gastric intestinal metaplasia antigen; and
(b) detecting immunoreactivity between the gastric tissue and the monoclonal antibody, such immunoreactivity indicating a positive diagnosis of human gastric intestinal metaplasia. The monoclonal antibody DAS-1 can differentiate at-risk groups of gastric intestinal metaplasia patients for gastric carcinoma.

The present invention also pertains to an in vivo immunoassay method for diagnosing human gastric intestinal metaplasia which comprises the steps of:
(a) administering to a human, suspected of having human gastric intestinal metaplasia, the monoclonal antibody DAS-1, or a fragment thereof, which monoclonal antibody is produced by the hybridoma deposited under ATCC accession number HB 9397 and which reacts with human gastric intestinal metaplasia antigen and is tagged with an isotope; and
(b) detecting immunoreactivity between the human gastric intestinal metaplasia cells and the monoclonal antibody by external scanning, such immunoreactivity indicating a positive diagnosis of human gastric intestinal metaplasia.

Preferably, the monoclonal antibody DAS-1 is administered to the human intravenously. Preferably, the human gastric intestinal metaplasia antigen is colon epithial specific protein.

In one embodiment, the monoclonal antibody DAS-1 is tagged with a radioisotope and immunoreactivity is detected by Immunoscintigraphy. Preferably, the radioactive isotope is $^{99}$Tc. In another embodiment, the monoclonal antibody DAS-1 is tagged with a stable isotope and immunoreactivity is detected by magnetic resonance imaging. Preferably, the stable isotope is selected from the group consisting of $^{2}$H, $^{13}$C, $^{15}$N, and $^{19}$F.

The method may further comprise the step of performing a negative control assay on a negative control sample to detect human gastric intestinal metaplasia cells present in the negative control sample and comparing results of the assay in (b) with the results of the negative control assay, wherein the presence of human gastric intestinal metaplasia cells in the assay in (b) above the presence of human gastric intestinal metaplasia cells in the negative control assay indicates a positive diagnosis of human gastric intestinal metaplasia. The method may also further comprise the step of performing a positive control assay on a positive control sample to detect human gastric intestinal metaplasia cells present in the positive control sample.

DETAILED DESCRIPTION OF THE INVENTION

A deposit of the monoclonal antibody DAS-1 (previously called 7E$_{12}$H$_{12}$, IgM isotype) has been made in the American Type Culture Collection, 10801 University Blvd., Manassas, Va. 20110-2209, and the deposited material has been accorded a specific accession number, namely HB9397.

This invention pertains to an in vitro immunoassay method for the diagnosis of human gastric intestinal metaplasia, a pre-cancerous condition. Specifically, the method comprises the steps of (a) contacting a gastric tissue sample of a subject suspected of having human gastric intestinal metaplasia cells with the monoclonal antibody DAS-1, or a fragment thereof, which monoclonal antibody is produced by the hybridoma deposited under ATCC accession number HB 9397 and which reacts with human gastric intestinal metaplasia antigen; and (b) detecting immunoreactivity between the gastric tissue and the monoclonal antibody, such immunoreactivity indicating a positive diagnosis of human gastric intestinal metaplasia. This invention also pertains to an in vitro immunoassay method for screening for human gastric intestinal metaplasia, thereby indicating a predisposition for gastric carcinoma. The monoclonal antibody DAS-1 can differentiate at-risk groups of gastric intestinal metaplasia patients for gastric carcinoma. This invention further pertains to an in vivo immunoassay method for diagnosing human gastric intestinal metaplasia. The method comprises the steps of (a) administering to a human, suspected of having human gastric intestinal metaplasia, the monoclonal antibody DAS-1, or a fragment thereof, which monoclonal antibody is produced by the hybridoma deposited under ATCC accession number HB 9397 and which reacts with human gastric intestinal metaplasia antigen and is tagged with an isotope; and (b) detecting immunoreactivity between the human gastric intestinal metaplasia cells and the monoclonal antibody by external scanning, such immunoreactivity indicating a positive diagnosis of human gastric intestinal metaplasia.

Gastric intestinal metaplasia (GIM) is considered a precursor lesion 10 in the development of intestinal-type of gastric cancer. However, it is unclear if gastric intestinal metaplasia of complete (small intestinal) or incomplete (colonic) phenotype predisposes gastric carcinogenesis. Such a phenotypic differentiation of gastric intestinal metaplasia has been difficult using a variety of histochemical stainings. A monoclonal antibody, mAB DAS-1 (previously called $7E_{12}H_{12}$, IgM 15 isotype) has been developed that reacts sensitively and specifically to colon and Barret's epithelium of the esophagus, which is a columnar metaplastic change at the gastroesophageal junction, and more recently, chronic cystitis profunda, a pre-cancerous condition of the urinary bladder and also adenoma of the small intestine. But the monoclonal antibody, mAB DAS-1 does not react with normal small intestinal, gastric, esophageal, and gastric-esophageal junctional epithelium. Using the monoclonal antibody, mAB DAS-1, histologically confirmed gastric intestinal metaplasia specimens (biopsy and surgical) from 2 Institutions were examined. Group A was gastric intestinal metaplasia from New Jersey patients with chronic gastric (without gastric carcinoma) (n=21). Group B was gastric intestinal metaplasia (away from cancer area) Japanese patients who were operated on for gastric carcinoma (n=35). Both groups were examined with mAb DAS-1 by the immunoperoxidase assay. Among the Japanese patients 30 of 35 were positive for *H. Pylori*. Seven of 18 (35%) samples from New Jersey, the glandular epithelium in gastric intestinal metaplasia clearly reacted with mAb DAS-1, whereas 11 did not. In contrast, 33 of 35 (94%) gastric intestinal metaplasia from gastric carcinoma patients reacted intensely with both goblet and non-goblet metaplastic cells with mAb DAS-1 (Group A vs. Group B, p<0.0001). Hence, the presence or absence of mAb DAS-1 reactivity in gastric intestinal metaplasia is useful to simplify and differentiate the phenotype in gastric intestinal metaplasia. Colonic phenotype of gastric intestinal metaplasia as identified by mAB DAS-1 appears to be strongly associated with gastric carcinoma.

Accordingly, our recent studies indicate that in patients with gastric intestinal metaplasia without gastric cancer the antibody mAB DAS-1 positively reacts with the gastric intestinal metaplasia in one third of the patients. However, in the gastric intestinal metaplasia of patients who had gastric carcinoma, the positive reactivity is 96% and this is statistically highly significant with the p value<0.0001. This finding strongly suggests a positive correlation of gastric intestinal metaplasia with gastric carcinoma and its reactivity to the monoclonal antibody mAB DAS-1. Therefore the reactivity with this antibody helps identify the patients with gastric intestinal metaplasia at risk group for gastric carcinoma. Such an identification of the patient will help to screen and follow those patients more closely by periodic endoscopic examination as well as for future development of chemo prevention programs to interfere with the development of gastric carcinogenesis. Thus, the antibody has a significant clinical value for the diagnosis of at-risk groups of gastric carcinoma. At this time, all patients with gastric intestinal metaplasia are considered to be in the at-risk group and periodic endoscopic examination is recommended. If the truly at-risk group can be identified, this will eliminate endoscopic examination of all of the patients with gastric intestinal metaplasia on a regular basis and in the long run will be very cost effective. Therefore, the use of this antibody to detect the at-risk group will also be economically useful.

As set out above, applicant has developed a monoclonal antibody, mAb DAS-1 ($7E_{12}H_{12}$, IgM isotype), that specifically reacts with colon epithelium and not with small intestinal enterocytes and many other epithelial organs (*J. Immunology* 1987:139;77). This hybridoma (mAb DAS-1) was obtained following the immunization of Balb/c mice with a human colonic protein extract highly enriched for p40, a putative colonic autoantigen in ulcerative colitis. Applicant has also shown that p40 could be either a colon-specific iso-form of tropomyosin (TM) or a tropomyosin related molecule (*J. Immunol*. 1993; 150:2487). To further delineate this relationship, the reactivity of mAB DAS-1 monoclonal antibody with various known isoforms of recombinant human tropomyosins (hTMs 1–5) derived from fibroblast was examined using ELISA and immunotransblot analysis. None of these 5 isoforms reacted with mAB DAS-1 monoclonal antibody. As determined by immunofluorescence and FACS analyses, mAB DAS-1 monoclonal antibody reacts with several colon cancer cells, namely DLD-1, LS180, T84, but not with HT-29 and many other non-colonic epithelial cells (293-T, HeLA, pancreatic cancer) and hematopoietic cells (K562, KGI, Daudi). Immunoprecipitation with mAB DAS-1 monoclonal antibody of $^{125}$I-labelled membrane proteins of DLD-1 revealed a consistent major band of 185 kDa, in addition to a minor band of the expected 40 kDa protein. DLD-1 cells grown with gamma interferon (10 $\mu$g/ml) increased the 185 kDa protein by 3 fold, indicating its amplification by the cytokine. To purify the mAB DAS-1-reactive protein, a membrane enriched fraction (MEF) of DLD-1 cells was used. The membrane enriched fraction was isolated by the standard methods, solubilized in detergents, and subjected to affinity chromatography using purified mAB DAS-1-IgM. Again, the predominant protein reactive to mAB DAS-1 was 185 kDa protein. The protein was purified to homogeneity by electroelution following SDS-PAGE. In addition, we have determined that this protein binds to various lectins, suggesting that it is a glycoprotein. More recently, using LS-180 colon cells, applicant has shown that the reactive protein to mAB DAS-1 in LS-180 colon cancer cells is a >200 kDa protein named colon epithelial protein (CEP) by immunotransblot analysis (Kesari et al., Clin Ex P Immunol 118:219 (1999). The difference in the molecular weight between CEP extracted from DLD-1 and LS-180 is probably due to differences in glycosylation. Furthermore, CEP acts as a chaperone protein in colon epithelial cells and binds with human tropomyosin 5 (hTM5) and forms a hTM5-CEP complex and both are released from colon epithelial cells.

The tropomyosins (TMs) are a large group of closely related actin-binding proteins present in all eukaryotic cells. These proteins are critical in the regulation of cytoskeletal structure and various functions related to cell motility. Eight distinct tropomyosin isoforms have been identified in human fibroblast cells. Classically, tropomyosins are known to be intracellular proteins and in the intestine they have been localized at the rootlet of brush border of microvilli by immunocytochemical staining. In experimental colitis and in patients with ulcerative colitis (UC), autoantibodies against tropomyosins have been demonstrated (*J. Immunol*. 1993; 150:2487). To elucidate how the autoantibody against this intracellular protein could be involved in the pathogenesis of ulcerative colitis, we have examined the presence of various isoforms of human tropomyosin (hTM) on the surface of the colonic epithelial cells and colon cancer cell lines. Isoform specific monoclonal antibodies (mAb) such as CGI (hTM1), CGβ6 (hTM2 and hTM3), CG3 (hTM5), were utilized for FACS analysis. Colon cancer cell lines included HT-29, DLD-I, LS180, T-84 and non-colon cell line was 293T. Cells were incubated with various antibodies on ice in PBS containing 0.1% sodium azide and 1% BSA, followed by appropriate FITC-conjugated antibodies. Cells were fixed in 1% formaldehyde and analyzed by FACS. Only one monoclonal antibody, CG3, (anti-hTM5) showed clear and strong reaction on the surface of the colonic epithelial cells, T84 and LS 180, and less strong on DLD-1. No reactivity was seen with HT-29 and 293 T cells. None of the other antibodies, including unrelated isotype control monoclonal antibodies reacted with any of the cell lines by FACS. These data indicate that a certain tropomyosin isoform (e.g., hTM5 or related protein) is expressed on the surface of the colon epithelial cells. Furthermore, both hTM5 and CEP were released in the LS-180 supernatant (Kesari et al., Clin Ex P Immunol 118:219 (1999).

We have further examined isoforms of human tropomyosins (hTMs) in isolated colonic epithelial cells from operative specimens of colon from patients with colon cancer, (normal segments), ulcerative colitis and Crohn's disease (CD). Human tropomyosin isoform specific monoclonal antibodies and recombinant human tropomyosins were utilized to examine the immunoreactivity by ELISA and by quantitative immunotransblot analysis. We demonstrated that hTM5 is the predominant TM in colon epithelial cells.

The antigen associated with human gastric intestinal metaplasia used in the present invention may be any antigen associated with human gastric intestinal metaplasia. Preferably, the antigen is reactive to monoclonal antibody mAB DAS-1, mAB DAS-1 reactive protein. More preferably, the colonic antigen is colon epithial specific protein (CEP).

The antibody which binds to an antigen associated with human gastric intestinal metaplasia with colonic phenotype used in the present invention may be any antibody. Preferably, the antibody is a murine antibody or a humanized antibody directed against the antigen. More preferably, the antibody is the monoclonal antibody mAB DAS-1.

Enzyme Immunoassay

A hybridoma which produces the monoclonal antibody of the present invention is obtained by carrying out cloning of the thus obtained antibody producing hybridoma by limiting dilution analysis or the like means. In order to produce the monoclonal antibody of the present invention in a large amount making use of the thus obtained hybridoma, as a first step; the cells are cultured in a large scale or, alternatively, pristane or the like mineral oil is administered into the abdominal cavity of mice, subsequently carrying out intraperitoneal administration of the hybridoma, and then the ascitic fluid is collected several days thereafter. Next, the monoclonal antibody is separated and purified from the thus obtained culture broth or ascitic fluid for example in accordance with the usual antibody separation purification techniques. The thus obtained monoclonal antibody of the present invention reacts with human gastric intestinal metaplasia.

The monoclonal antibody of the present invention produced by the hybridoma obtained in this manner can be classified as IgM isotype, but the antibody is not necessarily in its intact form after its production by the cells and may be in the form of Fab, F(ab)2, Fv or the like useful fragment. Such a useful fragment can be obtained from its original antibody by its peptidase hydrolysis using papain or pepsin. The term useful fragment means that it can bind to the binding site of the antigen of the same origin in competition with the original antibody. However, the above examples of the monoclonal antibody of the present invention are unique isotype antibodies which bind to specific determining sites on respective antigens and are derived from mice, though not particularly limited thereto. In consequence, the monoclonal antibody of the present invention which is derived from mouse, human or the like mammals or other origin or any combination thereof can be used, provided that the antibody has a function to bind to the specified specific determining site on the specified antigen in the same manner. Also, even when isotype of the antibody is IgG, IgA, IgE or the like other class, it can be used in the same manner.

Detection of Antigen

Measurement of the antigen of the present invention using an antibody specific for the antigen of the present invention can be carried out in accordance with known immunoassay methods, for example, to measure the presence of human gastric intestinal metaplasia, particularly precancerous phenotypes. The presence of human gastric intestinal metaplasia in a sample is confirmed by allowing the sample to react with the monoclonal antibody of the present invention and then detecting an immune complex linked to the sample. An example of the present invention is a method for the detection of human gastric intestinal metaplasia in biopsy tissues. A tissue section obtained by biopsy is fixed on a slide glass in the usual way. The thus obtained tissue section is allowed to react with the monoclonal antibody of the present invention. With regard to the reaction conditions, the reaction is carried out for example in an appropriate container such as a Petri dish. After removing non-specifically bound antibodies by washing, subsequent reaction is carried out with a second antibody which can react with the antibody and is labeled with a detectable marker. The marker is a substance which can generate a detectable signal, such as a radioactive element, a fluorescent material, an enzyme or the like. Since binding of the antibody reflects the presence of human gastric intestinal metaplasia of a specific phenotype, the presence of human gastric intestinal metaplasia can be confirmed by detecting the detectable signal. In addition, binding of the monoclonal antibody to a sample can also be measured by using the monoclonal antibody to which a radioactive material, an enzyme or the like marker capable of generating a detectable signal is linked by covalent bonding. Covalent bonding of a marker to the antibody or antibody fragment can be effected by a usually used method.

Immunoassays involve allowing proteins (human gastric metaplasia antigen) in a sample to bind to a solid phase support such as a plastic surface. Detectable antibodies are then added which selectively bind to the human gastric metaplasia antigen. Detection of the detectable antibody indicates the presence of human gastric metaplasia antigen. The detectable antibody may be a labeled or an unlabelled antibody. Unlabelled antibody may be detected using a second, labelled antibody that specifically binds to the first antibody or a second, unlabelled antibody which can be detected using labelled protein A, a protein that complexes with antibodies.

Simple immunoassays may be performed in which a solid phase support is contacted with the test sample. Any proteins present in the test sample bind the solid phase support and can be detected by a specific, detectable antibody preparation. Such a technique is the essence of the dot blot, Western blot and other such similar assays.

Other immunoassays may be more complicated but actually provide excellent results. Typical and preferred immunometric assays include "forward" assays for the detection of a protein in which a first anti-protein antibody bound to a solid phase support is contacted with the test sample. After a suitable incubation period, the solid phase support is washed to remove unbound protein. A second, distinct anti-protein antibody is then added which is specific for a portion of the specific protein not recognized by the first antibody. The second antibody is preferably detectable. After a second incubation period to permit the detectable antibody to complex with the specific protein bound to the solid phase support through the first antibody, the solid phase support is washed a second time to remove the unbound detectable antibody. Alternatively, the second antibody may not be detectable. In this case, a third detectable antibody, which binds the second antibody is added to the system. This type of "forward sandwich" assay may be a simple yes/no assay to determine whether binding has occurred or may be made quantitative by comparing the amount of detectable antibody with that obtained in a control.

Other types of immunometric assays are the so-called "simultaneous" and "reverse" assays. A simultaneous assay involves a single incubation step wherein the first antibody bound to the solid phase support, the second, detectable antibody and the test sample are added at the same time. After the incubation is completed, the solid phase support is washed to remove unbound proteins. The presence of detectable antibody associated with the solid support is then determined as it would be in a conventional "forward sandwich" assay. The simultaneous assay may also be adapted in a similar manner for the detection of antibodies in a test sample.

The "reverse" assay comprises the stepwise addition of a solution of detectable antibody to the test sample followed by an incubation period and the addition of antibody bound to a solid phase support after an additional incubation period. The solid phase support is washed in conventional fashion to remove unbound protein/antibody complexes and unreacted detectable antibody. The determination of detectable antibody associated with the solid phase support is then determined as in the "simultaneous" and "forward" assays. The reverse assay may also be adapted in a similar manner for the detection of antibodies in a test sample.

The first component of the immunometric assay may be added to nitrocellulose or other solid phase support which is capable of immobilizing proteins. The first component for determining the presence of human gastric metaplasia antigen receptor in a test sample is anti-human gastric metaplasia antigen receptor antibody. By "solid phase support" or "support" is intended any material capable of binding proteins. Well-known solid phase supports include glass, polystyrene, polypropylene, polyethylene, dextran, nylon, amylases, natural and modified celluloses, polyacrylamides, agaroses, and magnetite. The nature of the support can be either soluble to some extent or insoluble for the purposes of the present invention. The support configuration may be spherical, as in a bead, or cylindrical, as in the inside surface of a test tube or the external surface of a rod. Alternatively, the surface may be flat such as a sheet, test strip, etc. Those skilled in the art will know many other suitable "solid phase supports" for binding proteins or will be able to ascertain the same by use of routine experimentation. A preferred solid phase support is a 96-well microtiter plate.

To detect the presence of human gastric metaplasia antigen, detectable anti-receptor antibodies are used. Several methods are well known for the detection of antibodies.

One method in which the antibodies can be detectably labeled is by linking the antibodies to an enzyme and subsequently using the antibodies in an enzyme immunoassay (EIA) or enzyme-linked immunosorbent assay (ELISA), such as a capture ELISA. The enzyme, when subsequently exposed to its substrate, reacts with the substrate and generates a chemical moiety which can be detected, for example, by spectrophotometric, fluorometric or visual means. Enzymes which can be used to detectably label antibodies include, but are not limited to malate dehydrogenase, staphylococcal nuclease, delta-5-steriod isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. One skilled in the art would readily recognize other enzymes which may also be used.

Another method in which antibodies can be detectably labeled is through radioactive isotopes and subsequent use in a radioimmunoassay (RIA) (see, for example, Work, T. S. et al., Laboratory Techniques and Biochemistry in Molecular Biology, North Holland Publishing Company, N.Y., 1978, which is incorporated herein by reference). The radioactive isotope can be detected by such means as the use of a gamma counter or a scintillation counter or by autoradiography. Isotopes which are particularly useful for the purpose of the present invention are $^3H$, $^{125}I$, $^{131}I$, $^{35}S$, and $^{14}C$. Preferably $^{125}I$ is the isotope. One skilled in the art would readily recognize other radioisotopes which may also be used.

It is also possible to label the antibody with a fluorescent compound. When the fluorescent-labeled antibody is exposed to light of the proper wave length, its presence can be detected due to its fluorescence. Among the most commonly used fluorescent labeling compounds are fluorescein isothiocyanate, rhodamine, phycoerythrin, phycocyanin, allophycocyanin, o-phthaldehyde and fluorescamine. One skilled in the art would readily recognize other fluorescent compounds which may also be used.

Antibodies can also be detectably labeled using fluorescence-emitting metals such as $^{152}Eu$, or others of the lanthanide series. These metals can be attached to the protein-specific antibody using such metal chelating groups as diethylenetriaminepentaacetic acid (DTPA) or ethylenediaminetetraacetic acid (EDTA). One skilled in the art would readily recognize other fluorescence-emitting metals as well as other metal chelating groups which may also be used.

Antibody can also be detectably labeled by coupling to a chemiluminescent compound. The presence of the chemiluminescent-labeled antibody is determined by detecting the presence of luminescence that arises during the course of a chemical reaction. Examples of particularly useful chemoluminescent labeling compounds are luminol, isoluminol, theromatic acridinium ester, imidazole, acridinium salt and oxalate ester. One skilled in the art would readily recognize other chemiluminescent compounds which may also be used.

Likewise, a bioluminescent compound may be used to label antibodies. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin. One skilled in the art would readily recognize other bioluminescent compounds which may also be used.

Detection of the protein-specific antibody, fragment or derivative may be accomplished by a scintillation counter if, for example, the detectable label is a radioactive gamma emitter. Alternatively, detection may be accomplished by a fluorometer if, for example, the label is a fluorescent material. In the case of an enzyme label, the detection can be accomplished by colorometric methods which employ a substrate for the enzyme. Detection may also be accomplished by visual comparison of the extent of enzymatic reaction of a substrate in comparison with similarly prepared standards. One skilled in the art would readily recognize other appropriate methods of detection which may also be used.

The binding activity of a given lot of antibodies may be determined according to well known methods. Those skilled in the art will be able to determine operative and optimal assay conditions for each determination by employing routine experimentation.

Positive and negative controls may be performed in which known amounts of human gastric metaplasia antigen and no human gastric metaplasia antigen, respectively, are added to assays being performed in parallel with the test assay. One skilled in the art would have the necessary knowledge to perform the appropriate controls.

When an antibody specific for the antigen of the present invention is used, the antigen of the present invention in human tissue can be measured. This measurement can be carried out in accordance with a known immunoassay method. Examples of the antibody specific for the antigen of the present invention include both polyclonal and monoclonal antibodies which can be used alone or a combination thereof. Examples of the immunoassay include enzyme immunoassay, radioimmunoassay, radionuclide scan assay, fluoroimmunoassay, chemiluminescence/bioluminescence immunoassay, latex agglutination immunoassay and the like. As the enzyme immunoassay, optional known modifications can be used. For example, the antigen can be measured directly or competitively making use of a homogenous phase enzyme immunoassay, a solid phase method, a heterogeneous enzyme immunoassay, a sandwich enzyme immunoassay and the like. Of these methods, sandwich enzyme immunoassay is particularly desirable. In this method, a monoclonal antibody linked to a solid carrier is allowed to react with a test solution and then, after washing, a solution of an enzyme-labeled monoclonal or polyclonal antibody which has reactivity with the antigen is dispensed. After washing, amount of the antigen in the sample is measured based on the enzyme-substrate reaction. In this connection, the monoclonal antibody to be used in the latter reaction is desirably an antibody which can bind to a site which is different from the specific binding site recognizable by the monoclonal antibody linked to the solid carrier, except for a case in which the antigen has a plurality of sites to which the solid phase monoclonal antibody can be linked. Examples of the carrier to be used include a microplate, a test tube, beads or fine particles made of polystyrene, polyethylene or polyvinyl chloride, a test tube, beads or a filter paper made of glass, or a sheet of dextran, cellulose acetate or cellulose, as well as similar materials thereof. Also, examples of the desirable enzyme to be used in the enzyme immunoassay of the present invention include horseradish peroxidase, alkaline phosphatase, beta-galactosidase and the like. Examples of other assay methods of the present invention include radioimmunoassay in which a radioactive marker is used, fluoroimmunoassay in which a fluorescent marker is used, chemiluminescence/bioluminescence immunoassay in which a luminescent marker is used and latex agglutination immunoassay in which a latex marker is used Immunoscintigraphy Immunoscintigraphy (IS, or radioscintigraphy) is based on the principle that a specific radioactive-labeled antibody recognizes a defined epitope and is bound to this antigen. Since Koehler and Milstein introduced the hybridoma technique (Koehler G, Milstein C.; Nature 1975;256:494–7), various murine monoclonal antibodies have been manufactured. The clinical breakthrough, however, did not arise until Fab' fragments were developed (Goldenberg et al.; Eur J Nucl Med 1989;15:426). This fragment, an immunoglobulin of the IgGI fraction that had its Fc portion removed, is highly capable of targeting epitopes on the tumor surface. Because of its lack of antigenicity, it causes neither human antimouse antibody response nor any allergic reactions of unpredictable nature. The smaller molecular weight of the Fab' fragment compared with the intact murine antibody allows the fragment to leave the intravascular space and target the tumor earlier. 99 mTc, an isotope with a short physical half-life and high photon abundance, can be administered at high doses and allows early imaging with a gamma camera. It is very suitable for use in conjunction with a Fab' fragment, the half-life of which is also short. Immunoscintigraphy is discussed in detail in P. Lechner et al., Dis Colon Rectum 1993;36:930–935 and F. L. Moffet et al., J Clin Oncol 14:2295–2305 (1966), which disclosures are incorporated by reference herein.

In radioscintigraphy, a radioactive monoclonal antibody is typically injected into a patient for identifying and localizing a tumor, (reviewed in Bischof Delaloye, A. and Delaloye, B.: Tumor imaging with monoclonal antibodies. *Seminars in Nuclear Medicine* 25(2):144–164, 1995). In radioimaging with monoclonal antibodies, a chemically modified (chelate) form of a monoclonal antibody is typically prepared and stored as a relatively stable product. To be used clinically, however, the monoclonal antibody sample must be mixed with a radioactive metal, such as $^{99}$Tc, then purified to remove excess, unbound radioactive metal, and then administered to a patient within 6 hours, (Eckelman, W. C., Paik, C. H., and Steigman, J.: Three approaches to radiolabeling antibodies with $^{99}$Tc. *Nuc. Med. Biol.* 16: 171–176, 1989).

Magnetic Resonance Imaging (MRI)

Many diagnostic and therapeutic medical procedures for visualizing internal organs for the early detection and treatment of many diseases require the administration of contrast enhancing agents to improve the quality of the procedure. Contrast-enhancing agents are used in Magnetic Resonance Imaging (MRI). MRI provides a superior soft tissue differentiation than does Computerized Tomography. MRI procedures generally employ the nuclear magnetic resonance of hydrogen ($^1$H, usually of $H_2O$) or fluorine ($^{19}$F). The nuclear magnetic resonance sensitivity of $^{19}$F is nearly equivalent to that of $^1$H but the biological background of $^{19}$F is negligible. The usefulness of a contrast enhancing agent for diagnostic in vivo imaging depends upon the tissue-specificity of the agent, the ability to obtain sufficient signal intensity from the tissue-localized agent, and the requirement for a clear distinction of the signals from the imaging reagent from background MRI signals. In addition, the usefulness of the agent for medical imaging depends on the costs of preparing the agent, the ease of administering the agent, the toxicological and immunological properties of the agent, and the resistance to in vivo hydrolysis or decomposition of the agent.

In carrying out the present invention, it is desirable to prepare in advance an assay kit which comprises a combination of the monoclonal antibody of the present invention, the antigen of the present invention and other accessories.

For example, in the case of sandwich enzyme immunoassay, it contains a monoclonal antibody linked to an appropriate carrier, a freeze-dried preparation or a solution of an enzyme-labeled monoclonal antibody which can bind to the same antigen together with the monoclonal antibody or of a polyclonal antibody labeled with the enzyme in the same manner, a standard solution of purified antigen, a buffer solution, a washing solution, pipettes, a reaction container and the like. In this connection, the polyclonal antibody to be used in the assay of the present invention can be collected easily from an animal immunized against the antigen of the present invention in the usual way. For example, a rabbit is immunized several times using the antigen of the present invention, and when the antibody titer against the antigen reaches maximum, blood is collected to separate and purify the antibody fraction in the usual way.

The present invention is further illustrated by the following examples which are not intended to limit the effective scope of the claims. All parts and percentages in the examples and throughout the specification and claims are by weight of the final composition unless otherwise specified.

EXAMPLES

These examples illustrate the development of the monoclonal antibody mAB DAS-1 which is employed in an immunoassay method for the diagnosis of human gastric intestinal metaplasia.

Production of Monoclonal Antibody mAB DAS-1

In order to produce the mAB DAS-1 monoclonal antibody of this invention, six-week old BALB/c mice were immunized with an emulsion of 100 pg of a highly enriched Mr 40K protein (1 mg/ml) in an equal volume of complete Freund's adjuvant, given subcutaneously over the neck, in the footpad and intraperitoneally. The Mr 40K protein was purified from human colons. In order to produce the Mr 40K protein, human colon specimens were obtained within one-half hour of surgery for colectomy and stored in negative $-80°$ C. The colon extracts were normal segments which were removed from patients with colon cancer. The colon tissue was then thawed on ice and after removal of fats, the tissue was suspended in 50 ml of a buffer A containing 50 mM Tris HCl pH 8.0, 0.15M NaCl, 2 mM EDTA, 2 mM PMSF and a cocktail of protease inhibitors comprised of Aprotinine 0.3 $\mu$M, Pepstatin 1 pM, and Leupeptine 1 pM. The colon tissue was minced with a fine scissor and centrifuged at 2,000 g for 10 minutes, and the supernatant was discarded. The step was repeated at least 7 times until the supernatant was clear.

Next, 100 ml of buffer B (which is the same as buffer A, except that it contained 10 mM EDTA) was added to the final precipitate, and the precipitate was left on ice for half an hour and then homogenized over ice using a polytron for 5 minutes using 15 second bursts interspersed with one minute intervals. The homogenate was then centrifuged at 10,000 g for 30 minutes. The supernatant was removed and ultracentrifuged at 100,000 g for 90 minutes. Next, the supernatant was frozen and thawed 3 times and centrifuged for 10 minutes at 10,000 g to remove the precipitate. The supernatant was dialyzed against a buffer C containing 20 mM Bis-Tris Propane, pH 6.5 at 4° C.

Next, an ion exchange chromatography was performed using a DEAE column. The dialyzed material was delipidated by mixing it with an equal volume of 1, 1, 2-trichlorotrifluoroethane, vortexed and centrifuged at 2,000 g×30 minutes. The top aqueous layer was separated, filtered through 0.22 micron syringe filter and used for chromatography. Five mg of sample was loaded and the column was washed with buffer C until O.D. 280 absorption became steady near zero. Then the column was eluted with step gradient of 0.2M, 0.35M, and 0.48M NaCl in buffer C. Peaks were monitored by O.D. at 280 nm. The peaks were collected separately and dialyzed against a buffer D containing 20 mM phosphate and 0.15M NaCl, pH 7.4.

Hydrophobic Interaction Chromatography was then performed using the 0.35M and 0.48M NaCl eluates from the ion-exchange column. A 1×10 cm econo column (Bio-Rad) was packed with 5 ml bed volume of phenyl sepharose and equilibrated with 20 mM phosphate, 0.15M NaCl, pH 7.4 containing 0.8M ammonium sulfate. The protein sample was adjusted to 0.8M ammonium sulfate by addition of solid ammonium sulfate and loaded to the column as 1 mg of protein per ml of bed volume. The column was washed with loading buffer until the O.D. 280 steady near zero. Then, the column was eluted stepwise with 20 mM phosphate, 0.15M NaCl, pH 7.4 and then with distilled water.

Next, immunotransblot analysis was performed. Eluted proteins were subject to a 10% SDS polyacrylamide gel electrophoresis and electrophoretically transferred to nitrocellulose paper. The nitrocellulose strips were washed, dried and exposed for autoradiography at $-80°$ C.

After immunizing the mice with the highly enriched Mr 40K protein emulsion, the mice were given 40 $\mu$g of highly purified Mr 40K protein intravenously one day prior to fusion. The splenic lymphocytes were mixed with cells of non-secretor BALB/c-derived myeloma line (NSO) in the mid-logarithmic phase of growth in a ratio of 8:1 spleen to myeloma cells. Fusion was performed with a 50% polyethylene glycol (mol. wt. 4,000; Merck, Darmstadt, West Germany) using standard techniques.

After fusion, cells were washed once with HAT medium (100 pM hypoxanthine, 400 nM-aminopterin, 16 pM-thymidine 20% fetal calf serum, 10% NCTC109, 1% penicillin and streptomycin, 1% non-essential amino acids in DME) and gently resuspended at $5 \times 10^5$ myeloma cells/ml.

Cultures were set up with 100 $\mu$l of the suspension per well of 96-well flat-bottom plates (Linbro, Flow Laboratories Inc. McLean, Va.). Cultures were maintained at 37° C. in 8% $CO_2$ and screening for antibodies was performed on day 14 by an ELISA. Clonal growth was assessed by inspection. Positive clones were expanded in 24 well flat-bottom microculture plates (Linbro, Flow Laboratories, Inc., McLean, Va.) and cloned in soft agar. Expanded clones were maintained in vitro in 25 $cm^2$ flasks (Corning Glass Works, Corning, Yew York) or injected intraperitoneally into 2, 6, 10, 14 tetramethylpentadecane (Pristane; Aldrich Chemical Co., Milwaukee, Wis.)—primed BALB/c mice for the production of ascitic fluid. Aliquots of expanded clones were also frozen and stored in liquid nitrogen without subsequent loss of secretory capacity.

Of the monoclonal antibodies produced, the monoclonal antibody designated mAB DAS-1 gave the highest reactivity in the ELISA. The monoclonal antibody mAB DAS-1 was further purified by subcloning. The hybridoma secreting monoclonal antibody mAB DAS-1 is on deposit with the American Type Culture Collection, 10801 University Blvd., Manassas, Va. 20110-2209, where it was received Apr. 16, 1987 and catalogued as ATCC #HB9397.

Immunoassay Method for the Diagnosis of Human Gastric Intestinal Metaplasia

Using the monoclonal antibody, mAB DAS-1, histologically confirmed gastric intestinal metaplasia specimens (biopsy and surgical) from 2 Institutions were examined. Group A was gastric intestinal metaplasia from New Jersey patients with chronic gastric (without gastric carcinoma) (n=21). Group B was gastric intestinal metaplasia (away from cancer area) Japanese patients who were operated on for gastric carcinoma (n=35). Both groups were examined with mAb DAS-1 by the immunoperoxidase assay. Among the Japanese patients 30 of 35 were positive for *H. Pylori*. Seven of 18 (35%) samples from New Jersey, the glandular epithelium in gastric intestinal metaplasia clearly reacted with mAb DAS-1, whereas 11 did not. In contrast, 33 of 35 (94%) gastric intestinal metaplasia from gastric carcinoma patients reacted intensely with both goblet and non-goblet metaplastic cells with mAb DAS-1 (Group A vs. Group B, p<0.0001). Hence, the presence or absence of mAb DAS-1 reactivity in gastric intestinal metaplasia is useful to simplify and differentiate the phenotype in gastric intestinal metaplasia. Colonic phenotype of gastric intestinal metaplasia as identified by mAB DAS-1 appears to be strongly associated with gastric carcinoma.

Specifically, the tissues obtained were sectioned (Sum), mounted on poly-L-lysine coated slides, deparaffinized by heating at 56° C. for 1 hour, immersed in xylene, rehydrated in 100%, 95%, 70% and 50% alcohol and washed in phosphate buffered saline (PBS), pH 7.2. Free aldehydes were reduced with 0.05% solution borohydride in phosphate buffered saline, pH 7.2 for 30 minutes at 4° C. Sections were trypsinized (1% trypsin plus 1% $CaCl_2$ in phosphate buffered saline) for 15 minutes at 37° C., and washed in phosphate buffered saline for 5 minutes with three changes at 40° C. Sections were then sequentially reacted with 1% normal goat serum for 2 hours, monoclonal antibody DAS-1 at 1:10 to 1:50 dilution overnight at 4° C., washed and incubated with biotinylated goat anti-mouse IgM (Vector Lab, Burlingame, Calif.). The tissues were washed in phosphate buffered saline and then incubated with avidin-biotin-peroxidase complex (ABC, Vector Lab, Burlingame, Calif.) for 90 minutes. The reaction was then developed by treating with 1 mg/ml 3–3' diaminobenzidine (DAB) in 0.1 mol/1-TRIS-HCl buffer, pH 7.6, 0.02% $H_2O_2$ in the dark for 10 minutes. The tissues were then washed, stained in hematoxylin for one minute (for counterstaining), washed, dehydrated in graded (50%, 70%, 90% and 100%) ethanol and then in xylene for 2–3 minutes and mounted with coverslips for microscopic examination.

Accordingly, our studies indicate that in patients with gastric intestinal metaplasia without gastric cancer the antibody mAB DAS-1 positively reacts with the gastric intestinal metaplasia in one third of the patients. However, in the gastric intestinal metaplasia of patients who had gastric carcinoma, the positive reactivity is 96% and this is statistically highly significant with the p value <0.0001. This finding strongly suggests a positive correlation of gastric intestinal metaplasia of colonic phenotype with gastric carcinoma and its reactivity to the monoclonal antibody mAB DAS-1. Therefore the reactivity with this antibody helps identify the patients with gastric intestinal metaplasia at risk group for gastric carcinoma. Such an identification of the patient will help to screen and follow those patients more closely by periodic endoscopic examination as well as for future development of chemo prevention programs to interfere with the development of gastric carcinogenesis. Thus, the antibody has a significant clinical value for the diagnosis of at-risk groups of gastric carcinoma. At this time, all patients with gastric intestinal metaplasia are considered to be in the at-risk group and periodic endoscopic examination is recommended. If the truly at-risk group can be identified, this will eliminate endoscopic examination of all of the patients on a regular basis and in the long run will be very cost effective. Therefore, the use of this antibody to detect the at-risk group will also be economically useful.

Throughout this application, various publications have been referenced. The disclosures in these publications are incorporated herein by reference in order to more fully describe the state of the art.

While the invention has been particularly described in terms of specific embodiments, those skilled in the art will understand in view of the present disclosure that numerous variations and modifications upon the invention are now enabled, which variations and modifications are not to be regarded as a departure from the spirit and scope of the invention. Accordingly, the invention is to be broadly construed and limited only by the scope and spirit of the following claims.

I claim:

1. An in vitro immunoassay method for diagnosing human colonic type gastric intestinal metaplasia which comprises the steps of:
   (a) contacting a gastric tissue sample of a subject suspected of having human colonic type gastric intestinal metaplasia cells with a monoclonal antibody DAS-1, or a fragment thereof, wherein the monoclonal antibody is produced by a hybridoma deposited under ATCC accession number HB 9397 and reacts with a human gastric intestinal metaplasia antigen, wherein the antigen is a colon epithelial specific protein and wherein the gastric tissue sample is not a gastric cardia; and
   (b) detecting immunoreactivity between the gastric tissue sample and the monoclonal antibody, such immunoreactivity indicating a positive diagnosis of human colonic type gastric intestinal metaplasia.

2. The method according to claim 1, wherein the monoclonal antibody or the fragment thereof is directly attached to a detectable label.

3. The method according to claim 1, wherein detecting immunoreactivity is performed by an immunoperoxidase staining, an immunofluorescence, an immunoelectronmicroscopy, or an ELISA.

4. The method according to claim 1, wherein the immunoassay method is an immunoperoxidase staining.

5. The method according to claim 1, wherein the immunoperoxidase staining comprises:
   (a) deparaffinizing the gastric tissue by heating;
   (b) immersing the deparaffinized tissue in xylene;
   (c) rehydrating the tissue in decreasing concentrations of alcohol;
   (d) washing the rehydrated tissue in neutral PBS;
   (e) reducing the aldehydes of the washed tissue of step (d);
   (f) reacting the tissue with normal goat serum, the monoclonal antibody, biotinylated goat anti-mouse antibody and avidin-biotin-peroxidase complex;
   (g) treating the reacted tissue with diaminobenzidine;
   (h) washing the diaminobenzidine-treated tissue;
   (i) staining the washed tissue of step (h) with hematoxylin, eosin or both; and
   (j) examining the stained tissue under a microscope to detect the presence of immunoreactivity.

6. The method according to claim 5, which further comprises the step of trypsinizing the gastric tissue after reducing the aldehydes in the tissue but before reacting the tissue with the normal goat serum, the monoclonal antibody, biotinylated goat anti-mouse antibody and avidin-biotin-peroxidase complex.

7. The method according to claim 5, wherein the decreasing concentrations of alcohol used for rehydration are 100%, 95%, 70%, and 50% alcohol.

8. The method according to claim 1, further comprising the step of performing a negative control assay on a negative control sample and comparing results of the gastric tissue sample with the results of the negative control sample, wherein the presence of human colonic type gastric intestinal metaplasia cells in the gastric tissue sample over the absence of human colonic type gastric intestinal metaplasia cells in the negative control sample indicates a positive diagnosis of human colonic type gastric intestinal metaplasia.

9. The method according to claim 1, further comprising the step of performing a positive control assay on a positive control sample to detect human cells of colonic type gastric intestinal metaplasia present in the positive control sample.

10. An in vitro immunoassay method for screening for human colonic type gastric intestinal metaplasia, wherein reactivity with a monoclonal antibody DAS-1 is indicative of a predisposition for gastric carcinoma, which comprises the steps of:
   (a) contacting a gastric tissue sample of a subject suspected of having human colonic type gastric intestinal metaplasia cells with the monoclonal antibody DAS-1, or a fragment thereof, wherein the monoclonal antibody DAS-1 is produced by the hybridoma deposited under ATCC accession number HB 9397 and reacts with a human gastric intestinal metaplasia antigen, and wherein the gastric tissue is not a gastric cardia; and
   (b) detecting immunoreactivity between the gastric tissue and the monoclonal antibody, such immunoreactivity indicating a positive diagnosis of human colonic type gastric intestinal metaplasia.

11. The method according to claim 10 wherein the human gastric intestinal metaplasia antigen is a colon epithelial specific protein.

12. The method according to claim 11, wherein the monoclonal antibody or the fragment thereof is directly attached to a detectable label.

13. The method according to claim 11, wherein detecting immunoreactivity is performed by an immunoperoxidase staining, an immunofluorescence, an immunoelectromicroscopy, or an ELISA.

14. The method according to claim 11, wherein the immunoassay method is an immunoperoxidase staining.

15. The method according to claim 14, wherein the immunoperoxidase staining comprises:
   (a) deparaffinizing the gastric tissue by heating;
   (b) immersing the deparaffinized tissue in xylene;
   (c) rehydrating the tissue in decreasing concentrations of alcohol;
   (d) washing the rehydrated tissue in neutral PBS;
   (e) reducing the aldehydes of the washed tissue of step (d);
   (f) reacting the tissue with a normal goat serum, the monoclonal antibody, a biotinylated goat anti-mouse antibody and an avidin-biotin-peroxidase complex;
   (g) treating the reacted tissue with diaminobenzidine;
   (h) washing the diaminobenzidine-treated tissue;
   (i) staining the washed tissue of step (h) with hematoxylin, eosin or both; and
   (j) examining the stained tissue under a microscope to detect the presence of immunoreactivity.

16. The method according to claim 15, which further comprises the step of trypsinizing the gastric tissue after reducing the aldehydes in the tissue but before reacting the tissue with the goat serum, the monoclonal antibody, the biotinylated goat anti-mouse antibody and the avidin-biotin-peroxidase complex.

17. The method according to claim 16 wherein the decreasing concentrations of alcohol used for rehydration are 100%, 95%, 70%, and 50% alcohol.

18. The method according to claim 16, further comprising the step of performing a negative control assay on a negative control sample and comparing results of the gastric tissue sample with the results of the negative control sample, wherein the presence of human colonic type gastric intestinal metaplasia cells in the gastric tissue sample over the absence of human colonic type gastric intestinal metaplasia cells in the negative control sample indicates a positive diagnosis of human colonic type gastric intestinal metaplasia.

19. The method according to claim 16 further comprising the step of performing a positive control assay on a positive control sample to detect human cells of colonic type gastric intestinal metaplasia present in the positive control sample.

* * * * *